US006942849B2

(12) United States Patent
Neeser et al.

(10) Patent No.: US 6,942,849 B2
(45) Date of Patent: Sep. 13, 2005

(54) INCORPORATION OF EXOGENOUS LACTIC BACTERIA INTO THE ORAL MICROFLORA

(75) Inventors: Jean-Richard Neeser, Savigny (CH); Bernhard Guggenheim, Erlenbach (CH); Elena-Maria Comelli, Lausanne (CH); Francesca Stingele, Lausanne (CH); Pier Sandro Cocconcelli, Piacenza (IT)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/779,596

(22) Filed: Feb. 9, 2001

(65) Prior Publication Data

US 2002/0012637 A1 Jan. 31, 2002

Related U.S. Application Data

(63) Continuation of application No. PCT/EP99/05473, filed on Jul. 26, 1999.

(30) Foreign Application Priority Data

Dec. 8, 1998 (EP) .......................................... 98202707

(51) Int. Cl.$^7$ ................................................ A61K 7/28
(52) U.S. Cl. ................... 424/50; 435/252.1; 435/252.3; 435/252.9
(58) Field of Search ........................ 424/50; 435/252.1, 435/252.9, 252.3

(56) References Cited

U.S. PATENT DOCUMENTS

| 4,992,420 | A |   | 2/1991  | Neeser ............................ 514/8 |
| 5,032,399 | A |   | 7/1991  | Gorbach et al. ............... 424/93 |
| 5,358,858 | A |   | 10/1994 | Chiang et al. ............. 435/71.1 |
| 5,368,845 | A |   | 11/1994 | Gaffar et al. .................. 424/54 |
| 5,427,767 | A |   | 6/1995  | Kresse et al. ............... 424/93.2 |
| 5,427,769 | A |   | 6/1995  | Berrocal et al. ............... 424/54 |
| 5,494,664 | A |   | 2/1996  | Brassart et al. ............ 424/93.4 |
| 5,503,865 | A |   | 4/1996  | Behringer et al. ........... 426/587 |
| 5,756,665 | A |   | 5/1998  | Mollet et al. ................ 530/326 |
| 5,833,953 | A |   | 11/1998 | Berrocal et al. ............... 424/49 |
| 6,036,952 | A | * | 3/2000  | Oh |

FOREIGN PATENT DOCUMENTS

| EP | 0 524 732 A2 | 1/1993 |
| EP | 0 699 689 A1 | 3/1996 |
| JP | 59220191 | 12/1984 |
| JP | 4021633 A | 1/1992 |
| JP | 05004927 | 1/1993 |
| JP | 08256681 | 10/1996 |
| JP | 09084521 | 3/1997 |
| WO | WO 92/14475 | 9/1992 |
| WO | WO 94/12150 | 6/1994 |

OTHER PUBLICATIONS

Busscher et al. Streptococcus thermophilus and Its Biosurfactants Inhibit Adhesion by Candida spp. on Silicone Rubber. Applied and Environmental Microbiology (Oct., 1997) 63(10):3810–3817.*
Van Hoogmoed et al. The role of biosurfactants in affecting initial microbial adhesion mechanisms. Biofilms: Recent Advances in Their Study and Control (2000) 237–251. Editors: Evans, LV. Publisher: Harwood Academic Publishers, Amsterdam, Neth.*
Ahmady K. et al., "Distribution of Streptococcus mutans and Streptococcus sobrinus at Sub–Sites in Human Approximal Dental Plaque," Caries Res. 27:135–139, 1993.
Bentley R.W. et al., "Intrageneric Structure of Streptococcus Based on Comparative Analysis of Small–Subunit rRNA Sequences," International Journal of Systematic Bacteriology, 41:487–494, 1991.
Boumerdassi, H. et al., "Isolation and Properties of Lactococcus lactis subsp. lactis biovar diacetylactis CNRZ 483 Mutants Producing Diacetyl and Acetoin from Glucose," Applied and Environmental Microbiology, 63:2293–2299, 1997.
Frandsen E.V.G. et al., "Ecology of Viridans Streptococci in the Oral Cavity of Pharynx," Oral Microbiol. Immunol. 6:129–133, 1991.
Fujisawa, T. et al., "Taxonomic Study of the Lactobacillus acidophilus Group, with Recognition of Lactobacillus gallinarum sp. nov. and Lactobacillus johnsonii sp. no. and Synonymy of Lactobacillus acidophilus Grouop A3 (Johnson et al. 1980) with the Type Strain of Lactobacillus amylovorous," International Journal of Systematic Bacteriology, 42:487–491, 1992.
Gibbons R.J. et al, "Strains of Streptococcus mutans and Streptococcus sobrinus Attach to Different Pellicle Receptors," Infection and Immunity, 52:555–561, 1986.
Granato, D.A. et al., "A mouse monoclonal IgE antibody anti bovine milk β–lactoglobulin allows studies of allergy in the gastrointestinal tract," Clin. exp. Immunol. 63:703–710, 1986.
Hiroi T. et al., "De novo glucan synthesis by mutans streptococcal glucosyltransferases present in pellicle promotes firm binding of Streptococcus gordonii to tooth surfaces," FEMS Microbiology letters 96:193–198, 1992.

(Continued)

Primary Examiner—Kathleen Kerr
(74) Attorney, Agent, or Firm—Bell, Boyd & Lloyd LLC

(57) ABSTRACT

The present invention provides compositions for the prophylaxis or treatment of dental caries, dental plaque, and periodontal infection that include lactic bacteria that are not part of the resident micriflora of the mouth, that are low acidifying, and that are capable of adhering directly to the pellicle of the teeth. Preferably, the lactic bacteria of the include one or more of Streptococcus thermophilus, Lactococcus lactis subsp. lactis, or Lactococcus lactis subsp. lactis biovar diacetylactis. The compositions are used in methods of treating or preventing dental caries, dental plaque, and periodontal infection.

10 Claims, 2 Drawing Sheets

OTHER PUBLICATIONS

Ito Y. et al., "Cloning and Nucleotide Sequencing of I–Lactate Dehydrogenase Gene from *Streptococcus thermophilus* M–192," Biosci. Biotech. Biochem. 58:1569–1573, 1994.

Kolenbrander P.E., "Coaggregations among Oral Bacteria," Methods in Enzymology 253:385–397, 1995.

Lindquist B. et al., "Dental Location of *Streptococcus mutans* and *Streptococcus sobrinus* in Humans Harboring Both Species," Caries Res. 25:146–152, 1991.

Lindquist B. et al., "Distribution and Prevalence of Mutans Streptococci in the Human Dentition," J. Dent Res. 69(5):1160–1166, 1990.

Meurman J.H. et al., "Recovery of *Lactobacillus* Strain GG (ATCC 53103) from Saliva of Healthy Volunteers after Consumption of Yoghurt Prepared with the Bacterium," *Microbial Ecology in Health and Disease* 7:295–298, 1994.

Perdigon G. et al., "Systemic augmentation of the immune response in mice by feeding fermented milks with *Lactobacillus casei* and *Lactobacillus acidophilus*,"Immunology 63:17–23, 1988.

Perdigon G. et al., "Actividad Immunopotenciadora De Bacterias Lacticas Adminitradas Por Vial Oral," Medicina 46:751–754, 1986. (non–English).

Platteeuw C. et al., "Metabolic Engineering of *Lactococcus lactis:* Influence of the Overproduction of α–Acetolactate Synthase in Strains Deficient in Lactate Dehydrogenase as a Function of Culture Conditions," Applied Environmental Microbiology 61(11):3967–3971, 1995.

Schüpbach P. et al., "Incorporation of Caseinoglycomacropeptide and Caseinophosphopeptide into the Salivary Pellicle Inhibits Adherence of Mutans Streptococci," J. Dent Res 75(10):1779–1788, 1996.

Skopek R.J. et al., "The influence of saliva on interbacterial adherence," Oral Microbiol Immunol 9:19–24, 1994.

Tanzer J.M. et al., "Competitive Displacement of Mutans Streptococci and Inhibition of Tooth Decay by *Streptococcus salivarius* TOVE–R," Infection and Immunity, 44–50, 1985.

* cited by examiner

INCORPORATION OF EXOGENOUS LACTIC BACTERIA INTO THE ORAL MICROFLORA

CROSS REFERENCE TO RELATED APPLICATIONS

This application is a continuation of the U.S. national phase designation of PCT application no. PCT/EP99/05473, filed Jul. 26, 1999, the entire contents of which are incorporated herein by reference thereto.

FIELD OF THE INVENTION

The present Invention relates to the incorporation of exogenous lactic bacteria into the oral microflora for the prophylaxis or the treatment of dental caries, dental plaque, and periodontal infection.

BACKGROUND OF THE INVENTION

The mouth (oral cavity) contains resident and non-resident microflora. The resident microflora includes microorganisms that are able to establish a more or less permanent residence on the oral surfaces. These bacteria are mainly localized on the tongue, the buccal mucosa, and the teeth while the gingiva, lips, checks, palate, and floor of the mouth only support a very sparse microflora.

On the tongue and the buccal mucosa, the natural resident microflora includes microorganisms selected from Streptococcus, Veillonella, Bacteroides, and Haemophilus. On the teeth, Streptococcus, Lactobacillus and Actinomyces predominate but a variety of Gram positive and negative cocci and rods can be also found.

For example, Frandsen et al. showed that S. sanguis predominates on the buccal mucosa but its primary habitat is the surface of teeth, that S. gordonji grows in the mature supragingival plaque, and that S. oralis and S. mitis grow in the initial dental plaque (Oral Microbiol. Immunol., 6, 129–133, 1991). Strains belonging to the mutans group are localized on teeth (S. criscetus, S. downei, S. ferus, S. macacae, S. mutans, S. rattus, S. sobrinus). Strains belonging to the S. milleri group predominate in dental abscesses (S. anginosus, S. constellatus, S. intermedius) (Bentley et al., Int. J. System. Bacter. 1991, 41, 487–494; Wood et al., The Genera of Lactic Acid Bacteria, Blackie Academic and Professional, Chapman & Hall, W. H. eds., 1995).

Many of these microorganisms are innocuous commensal microorganisms, but a lot of them have been recognized as being the etiologic agent responsible for several diseases (Hill, M. J. and Marsh, P. D. eds. Human Microbial Ecology, 1990, CRC Press. Boca Raton Fla., USA)

Dental plaque is a film that forms on the surface of teeth consisting of bacterial cells in a matrix of extracellular polysaccharide and salivary products. Immediately after eruption, the teeth are covered with an amorphous layer of saliva, the acquired enamel pellicle (AEP), that is about 1.3 μm thick and cannot be removed by normal tooth brushing. The deposition of bacteria on teeth immediately follows the formation of the AEP and plaque becomes evident in 8–12 hours as a multi-layered structure. The first layer consists of bacteria (earliest colonizers) that attach to teeth, mainly via specific adhesion-receptor recognition, and forms a substratum for the second colonizers that adhere one to the other by analogous specific binding or by simple juxtaposition. Plaque cohesion is essentially guaranteed by three mechanisms: the presence of a salivary pellicle on the outer bacteria layer, the specific coaggregation among the different bacterial species, and the glucans synthesized by the bacteria that remain entrapped in the plaque matrix (Skopek et al., Oral Microbiol. Immunol., 2, 19–24, 1994; Kolenbrander et al., Meth. Enzymol., 253, 385–397, 1995; Hiroi et al., FEMS Microbiol Lett., 96, 193–198. 1992; Gibbons et al., Infect. Immun., 52, 555–561, 1986).

The organic acids produced by oral bacteria during the fermentation process directly cause dental caries. These acids attack the hard tissue of teeth with the consequent release of ions such as calcium, phosphate, carbonate, magnesium, fluoride, and sodium. When the pH in the oral cavity again increases to around neutrality, the saliva becomes saturated with calcium so that calcium liberation from the tooth is prevented. Among all the food residues found in the mouth, carbohydrates show the highest caries promoting effect since they are directly available for fermentation by oral bacteria.

Potentially all microorganisms that ferment sugars are cariogenic, but the primary etiological agents of coronal and root caries are the mutans streptococci because they are strong acid producers; Lactobacilli, that are highly aciduric, however, can also be implicated. In humans, S. mutans and S. sobrinus are the more cariogenic strains, and live on teeth while not colonizing the entire dentition. Their number is also less on anterior teeth than on molar teeth (Lindquist et al., Dent. Res., 69, 1160–1166, 1990). Moreover in human approximal plaque, S. mutans and S. sobrinus preferentially colonize the most caries-prone site apical to the contact area (Ahmady et al., Caries Res., 27, 135–139, 1993). A higher prevalence of S. sobrinus was also found in the molar regions compared with that of S. mutans (Lindquist et al., Caries Res., 25, 146–152, 1991).

S. mutans and S. sobrinus have been shown to attach to the pellicle of teeth mainly via specific adhesion-receptor interaction. Gibbons et a). showed that S. mutans carries an adhesion which binds to salivary components in the pellicle, while S. sobrinus cells appear to possess an adhesion which binds to glucan in the pellicle (Infect. Immun., 52, 555–561, 1986).

The transient microflora comprise exogenous bacteria that are occasionally present in the mouth, but that do not establish a permanent residence therein (even if repeated oral administrations of these bacteria are carried out). All the food bacteria, and in particular lactic acid bacteria, can be part of this transient microflora. These exogenous lactic bacteria have never been shown to be capable of directly adhering to the pellicle of teeth. Repeated administration of exogenous lactic bacteria may, however, lead to colonization of the mouth on all the oral surfaces, such as the tongue, the buccal mucosa, the gingiva, lips, cheeks, palate, floor, and the teeth. This colonization may result from attachments via specific bindings to bacteria of the resident micro flora (co-aggregation phenomena), via entrapment in the matrix of polysaccharide produced by the resident bacteria, or via adhesion to saliva proteins (especially glycoproteins).

Lactobacillus casei rhamnosus GG (ATCC53103) has been reported to colonize the mouth, most probably on the epithelium of the buccal mucosa. This strain also adheres to the epithelium of the intestinal tract (U.S. Pat. No. 5,032, 399, Gorbach et al.; Micr. Ecol. In Health and Dis., 2, 295–298, 1994). By contrast L. rhamnosus does not adhere to teeth.

Japanese patent no. 4021633 (Cyconmedix KK) also reported colonization of the mouth by Lactobocillus acidophilus, most probably on the epithelium of the buccal mucosa. Many Lactobacillus acidophilus are known to also adhere to the epithelium of the intestinal tract (EPS77904;

EP199535; Perdigon et al., Medicina, 46, 751–754, 1986; Perdigon et al., Immunology, 63, 17–23, 1988).

Exogenous bacteria can also produce factors that inhibit the growth of the resident microflora in the mouth. For example, EP759469 (Société des Produits Nestlé) described the use of a bacteriocin produced by *Micrococcus varians* for inhibiting the development of the oral pathogens *S. sobrinus*, *S. sanguis*, *S. mutans*, and *A. viscous*.

There are several strategies to minimize the development of resident microflora of the mouth. For example, by administering commensal bacteria of the resident microflora that are not cariogenic, such as *Streptococcus salivarius* and/or *Stomatococcus mucilaginosus*, and/or repeated administration of exogenous lactic bacteria such as *L. casei, L. fermentum, L. acidophilus, L. crispatus, L. gasseri, L. salivarius, L. bulgaricus*, and *S. salivarius* (Tanzer et al., Infec. and Immunity, 48, 44–50, 1985; WO92/14475).

The application of bacteriocins is another investigated strategy which has been used to reduce tooth caries. These molecules have attracted interest as prospective anti-carie agents and as factors important in modulating colonization of the oral cavity. The anti-carie potential of applying bacteriocins comes from their potent and broad antibacterial activity against mutans streptococci and bacteria associated with dental plaque and their natural occurrence in bacteria regarded as being safe to humans (U.S. Pat. No. 5,368,845 to Colgate, and WO 94/12150 to Smithkline Beecham).

The application of milk derivatives is also of interest for the health of the mouth. Indeed, U.S. Pat. No. 5,427,769 (Nestec S.A.) describes another alternative wherein dental caries are prevented by contacting teeth with an edible composition containing micellar casein in amount sufficient to inhibit colonization by *Streptococcus sobrinus*. EP748591 (Société des Produits Nestlé S.A.) also reports the use of fluoridated micellar casein or its micellar subunits for treating dental caries or plaque. U.S. Pat. No. 4,992,420 (Nestec S.A.) describes treatment of the buccal cavity with kappa-caseino-glycomacropeptide derived from milk for eradicating plaque and caries.

Lactic bacteria that are not part of the resident microflora of the mouth have never been shown to be really capable of directly adhering to the pellicle of teeth. By colonizing the surface of teeth, however, such lactic bacteria could exert an inhibitory activity against the growth of the resident microflora, including oral pathogens.

SUMMARY OF THE INVENTION

The present invention is directed to a method of treating or preventing dental caries, dental plaque, and periodontal infection in a humans or animals comprising administering to the oral cavity or a human or animal one or more lactic bacteria that are not part of the resident microflora of the mouth, that are low acidifying, and that are capable of adhering directly to the pellicle of the teeth to displace from the teeth or prevent attachment to the teeth of cariogenic strains of bacteria that are resident microflora of the mouth. In one embodiment the lactic bacteria to be administered provides a pH in the oral cavity of about 5.5 to 5.7. Advantageously, the lactic bacteria may be of dairy origin.

The lactic bacteria is preferably one or more of *Strepro- coccus thermophilus, Lactococcus lactis* subsp. *lactis*, or *Lactococcus lactis* subsp. *lactis biovar diaceytlactis*. In particular the lactic bacteria is one of the strains CNCM I-1984, CNCM I-1985, CNCM I-1986, CNCM I-1987, and LMG P-18997.

Preferably, the lactic bacteria has optimal growth at a temperature of about 37° C., i.e., the temperature of the mouth. The lactic bacteria may have been genetically modified to have improved adherence to the pellicle of the teeth or to be less acidifying than resident microflora found in the mouth. The lactic bacteria may be genetically modified to have improved adherence to the pellicle of the teeth by insertion of the genes of GenBank Accession number X17390, GenBank Accession number X14490, or GenBank Accession number X53657.

In another embodiment the method of the invention further involves administering the lactic bacteria in combination with one or more of milk, fermented milk, milk derivatives, or bacteriocin. The milk derivative may be one or more of a caseino-glycomacropeptide, micellar casein, fluorinated micellar casein, or renneted milk.

The invention also relates to dental compositions for use in the methods of the invention. The lactic bacteria may be present in these compositions in an amount of $10^4$ to $10^9$ cfu/g in order to provide a pH of at least 5.5 when the composition is administered to the mouth of a human or animal. When bacteriocin is present in an the composition, it is typically present in an mount of 0.00001 to 50 percent by weight of the composition. When the milk derivative is one or more of a caseino-glycomacropeptide, micellar casein, fluorinated micellar caesin, or renneted milk it may be present in an amount of at least about 0.1 percent by weight of the composition. The composition may further include one or more of an oil soluble antioxidant in an amount of about 0.005 to 0.5 percent by weight of the composition and an abrasive. The composition may be in the form of a toothpaste, mouth rinse, gum, spray, beverage, candy, infant formula, ice cream, frozen dessert, sweet salad dressing, milk preparation, cheese, quark, yogurt, acidified milk, coffee cream, or whipped cream.

The invention also relates to a method for screening lactic bacteria capable of adhering to teeth. The method involves the steps of preparing monoclonal antibodies that recognize specific surface proteins of lactic bacteria strains that are capable of adhering to the teeth and screening lactic bacteria strains with the monoclonal antibody to identify the strains of lactic bacteria that adhere to teeth.

DETAILED DESCRIPTION OF THE INVENTION

Figure 1A:
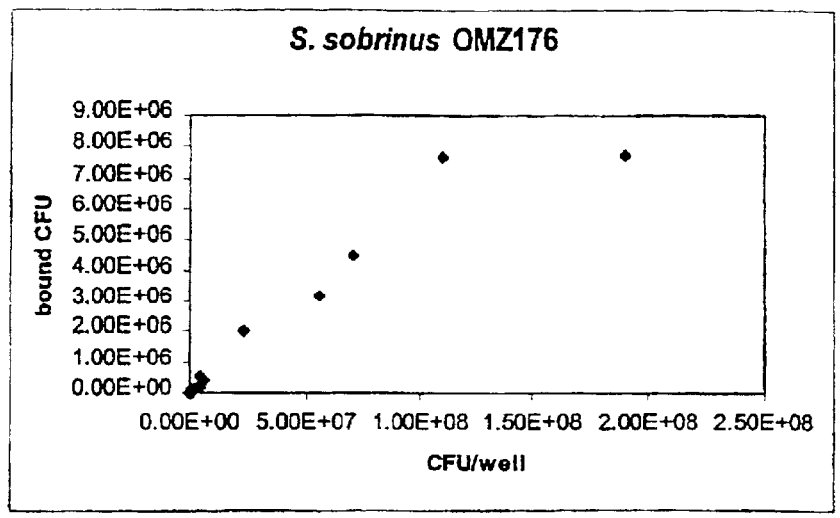
FIG. 1 represents the adhesion saturation curves for *S. sobrinus* OMZ 176 (1a), *L. lactis* NCC2211 (1b), and *S. thermophilus* NCC1561 (1c)

The object of the present invention is to use lactic bacteria that are not part of the resident microflora of the mouth, that is lactic bacteria that are low acidifying and that are capable of adhering directly to the pellicle of the teeth, to prepare a composition intended for the prophylaxis or the treatment of dental caries, dental plaque, and periodontal infection.

In one embodiment of the invention the lactic bacteria have been genetically modified to increase its adherence to the pellicle of the teeth via adhesion factors and/or genetically modified to be even less acidifying, contributing to a pH in the oral cavity of about 5.5 to 7.

The lactic bacteria may be selected from the group consisting of:
- an acidifying lactic bacteria that adheres to the pellicle of the teeth and that has been genetically modified so that it is low acidifying compared to resident microflora;
- a non adherent lactic bacteria that is low acidifying and that has been genetically modified so that it adheres to the pellicle of the teeth;
- a non-adherent acidifying lactic bacteria that has been genetically modified so that it adheres to the pellicle of the teeth and genetically modified so that it is low acidifying compared to resident microflora.

In another embodiment the bacteria, that is not part of the resident microflora, is low acidifying compared to resident microflora and is capable of adhering directly to the pellicle of the teeth.

In another embodiment the composition for the health of the mouth comprises (I) at least a lactic bacteria that is not part of the resident microflora of the mouth, which is capable of adhering directly to the pellicle of the teeth and contributing to a pH in the oral cavity of above 5.5, and (2) any form of caseinoglycomacropeptide, micellar casein, fluorinated micellar casein, renneted milk, or bacteriocin.

The invention also provides a method for screening lactic bacteria capable of adhering to tooth. The method comprises the steps of: (1) preparing monoclonal antibody recognizing specific surface proteins of a lactic bacteria strain capable of adhering to the teeth, and (2) screening any lactic bacteria strain by use of the monoclonal antibody of strain capable of adhering to the teeth.

The term "mouth," as used herein defines the oral cavity of humans or animals such as pets, composed by the oral mucosa (gums, lips, checks, palate, and floor of the mouth), the tongue, and the teeth (including artificial structures).

Resident microflora of the mouth includes all microorganisms that naturally live in the mouth because they can establish a permanent residence on the oral surfaces. The resident microflora of the mouth also includes bacteria that live in the interfacial region between the dental hard and soft tissues (the junction tooth-gingiva), even thought the gingival crevice and the periodontal pocket are not present in a healthy mouth. This microflora includes microorganisms selected from *Streptococcus, Staphylococcus, Enterococcus, Micrococcus, Peptostreptococcus, Peptococcus, Lactobacillus, Corynebacterium, Actinomyces, Arachnia, Rothia, Alcaligenes, Eubacterium, Propionibacterium, Bifidobacterium, Bacillus, Clostridium, Neisseria/Branhamella, Veillonella, Enterobacteriaceae, Campylobacter, Eikenella, Actinobacillus, Capnocytophga, Haemophilus, Simonsiella, Bacteroides, Fusobacterium, Porphyromonas, Prevotella, Leptotrichia, Wohlinella/Selenomonas, Mycoplasma, Candida, Spirochaetes, Protozoa.*

Transient microflora comprises exogenous bacteria that can be occasionally present in the mouth, but that do not establish a permanent residence. This transient microflora may comprise all the food micro-organisms, such as the bifidobacteria (*B. infantis, B. adolescentis, B. brewe* and *B. longum*): the *lactococci* (*Lactococcus lactis* subsp. *lactis, Lactococcus lactis* subsp. *cremoris,* and *Lactococcus lactis* subsp. *lactis biovar diacetylactis*): the *streptococci* (*Streptococcus thermophilus, S. lactis, S. lactis cremoris* and *S. lactis diacetylactis*); the *Lactobacilli* (*Lactobacillus delbrueckii* subsp. *bulgaricus, Lactobacillus helveticus, Lactobacillus farciminis, Lactobacillus alimentarius, Lactobacillus casei* subsp. *casei, Lactobacillus delbruckii* subsp. *lactis, Lactobacillus sake, Lactobacillus curvatus, Lactobacillus fermentum;* and the acidophile group comprising *L. johnsonii,* (see Fujisawa et al., Int. J. Syst. Bact., 42, 487–491, 1992); the *pediococci* (*Pediococcus pentosaceus, Pediococcus acidilactici,* and *Pediococcus halophilus*): the *enterococci;* the *staphilococci* (*Staphylococcus xylosus* and *Staphylococcus carnosus*): the *micrococci* (*Micrococcus varians*): yeast of the genus *Debaromyces, Candida, Pichia, Torulopsis and Saccharomyces;* and mold of the genus *Aspergillus, Rhizopus, Mucor* and *Penicillium.*

The lactic bacteria according to the invention that are low acidifying and capable of adhering directly to the pellicle of the teeth that are used to prepare compositions for the prophylaxis or the treatment of dental caries, dental plaque, and periodontal infection displace pathogenic bacteria from the teeth or prevent the attachment of the pathogenic bacteria. The lactic bacteria according to the invention are "low acidifying," which means that they are less acidifying than pathogenic strains. Accordingly, they contribute to a pH in the oral cavity of about 5.5 to 7. Preferably, they are from dairy origin.

The lactic bacteria according to the invention adhere to the pellicle of the teeth via specific or unspecific interactions and/or adhesion factors. The specific adhesion factors are proteins or polysaccharides.

At least one lactic bacteria is selected from the group consisting of *Streptococcus thermophilus, Lactococcus lactis* subsp. *lactis,* and *Lactococcus lactis* subsp. *Lactis biovar diacetylactis* and particularly from the group consisting of the strains CNCM 1-1984, CNCM 1-1985, CNCM 1-1986, CNCM 1-1987, and LMG P-18997. These strains have been selected among lactic bacteria strains for their capacity to adhere to the pellicle of the teeth and their optimal growth temperature of about 37° C., which is the temperature in the oral cavity. Moreover they are capable of fermenting glucose and sucrose and do not synthesize glucans, which are factors leading to the pathogenicity of the cariogenic strains.

In one embodiment of the invention the lactic bacteria are genetically modifying so that they adhere to the pellicle of the teeth via adhesion factors. For lactic bacteria that already adhere to the pellicle of the teeth, this modification makes the strains more adherent to the surface of the teeth. In the same way, any non-adherent lactic acid bacteria (not Lactobacilli) can be genetically modified so that it adheres to the pellicle of the teeth. This modification of the lactic bacteria can be achieved, for example, by insertion of the genes X17390, X14490 or X53657 (GenBank accession numbers). These gene are responsible in *S. mutans* for the expression of the Antigen I/II that mediates adhesion to salivary glycoproteins.

According to the invention, it is also possible to genetically modify lactic bacteria so that they are low acidifying. For lactic bacteria that is already low acidifying this modification increases the effect by further decreasing lactic acid production. This modification can be achieved in many ways. Preferably, the modification is achieved according to one the protocols described in the following documents: Boumerdassi et al., Appl. Environ. Microbiol., 63, 2293–2299, 1997; Plattecuw et al., Appl. Environ. Microbiol, 61, 3967–3971, 1995; Ito et al., Biosci. Biotechnol. Biochem., 58, 1569–1573, 1994.

According to the invention, at least one lactic bacteria, genetically modified or not, is used in an "effective amount" for the preparation of compositions intended for the prophylaxis or the treatment of dental caries, dental plaque, and periodontal infection in humans or animals such as pets. This quantity is preferably between $10^4$ to $10^9$ cfu/g.

It is also possible to use the at least one lactic bacteria, in combination with milk derivatives, such as milk, fermented milk, or milk derivatives selected from any forms of caseino-glycomacropeptide, micellar casein, fluorinated micellar casein, renneted milk, or bacteriocin, for example.

Biochemical Characterization of the Selected Strains

Fermentation patterns: 49 simple sugars were tested with the api 50 CH bioMerieux strip test (bioM6rieux SA, 69280 Marcy-l'Etoile, France). The results are given in the Table 1.

Acidification curves: Acidification curves were determined at 37° C. under the following conditions:

S. sobrinus OMZ 176: FUM sucrose 1% and FUM glucose 1%

S. thermophilus CNCM 1-1985: Belliker sucrose 1% and Belliker glucose 1% Inoculation was always 5%. The pH was recorded every 20 min.

S. thermophilus CNCM 1-1985, from sucrose fermentation, lowers the pH to 4.5, while S. sobrinus OMZ 176 lowers the pH to 4.

TABLE I

Sugar fermentation of *L. lactis* CNCM I-1987, *L. lactis* CNCM I-1986, *S. thermophilus* CNCM I-1984, *S. thermophilus* CNCM I-1985 and, *S. thermophilus* LMG P-18997.

| Sugar | L. lactis CNCM I-1987 | L. lactis CNCM I-1986 | S. th. CNCM I-1984 | S. th. CNCM I-1985 | S. th. LMG P-18997 |
|---|---|---|---|---|---|
| Adonitol | +++ | | | | |
| Aesculin | ++ | ++++ | | | |
| Amygdalin | ++++ | | | | |
| D-Arabinose | | | | | |
| L-Arabinose | | | | | |
| D-Arabitol | | | | | |
| L-Arabitol | +++ | | | | |
| Arbutin | +++ | +++ | | | |
| Cellobiose | +++ | +++ | | | |
| Dulcitol | | | | | |
| Erythritol | | | | | |
| D-Fructose | + | ++++ | | | |
| D-Fucose | | | | | |
| L-Fucose | | | | | |
| Galactose | ++ | ++++ | | | |
| β-Gentiobiose | | +++ | | | |
| Gluconate | | | | | |
| 2-keto-Gluconate | | | | | |
| 5-keto-Gluconate | | | | | |
| GlcNAc | + | ++++ | | | |
| D-Glucose | + | ++++ | + | ++ | ++ |
| Glycerol | | | | | |
| Glycogen | | | | | |
| Inositol | | | | | |
| Inulin | | | | | |
| Lactose | + | ++++ | +++ | ++++ | ++++ |
| D-Lyxose | | | | | |
| Maltose | ++ | | | | |
| Mannitol | +++ | ++ | | | |
| D-Mannose | + | ++++ | | | |
| Melezitose | | | | | |
| Melibiose | | | | | |
| α-Methyl-D-glucoside | | | | | |
| α-Methyl-D-mannoside | | | | | |
| D-Raffinose | | | | | |
| Rhamnose | | | | | |
| Ribose | ++ | ++ | | | |
| Salicin | +++ | +++ | | | |
| Sorbitol | | | | | |
| L-Sorbose | | | | | |
| Starch | | | | | |
| Sucrose | | | +++ | ++++ | +++ |
| D-Tagatose | | | | | |
| Trehalose | ++ | | | | |
| D-Turanose | ++ | | | | |
| Xylitol | +++ | | | | |
| D-Xylose | | | | | |
| L-Xylose | | | | | |
| β-methil-xyloside | | | | | |

+, ++, +++, ++++ show if the fermentation begins after 3, 6, 24, or 48 hours, respectively.

The invention is also directed to compositions for the health of the mouth that comprise a lactic bacteria that is not part of the resident microflora of the mouth, that is low acidifying, and that is capable of adhering directly to the pellicle of the teeth. The compositions are particularly intended for the prophylaxis or the treatment of dental caries, dental plaque, and periodontal infection. The lactic bacteria strain may be selected from the group consisting of *Streptococcus thermophilus, Lactococcus lactis* subsp. *lactis,* and *Lactococcus lactis* subsp. *lactis biovar diacetylactis* and preferably from the group consisting or the strains CNCM I-1984, CNCM I-1985, LMG P-18997, CNCM I-1986, and CNCM I-1987. In these compositions the lactic bacteria strains may be genetically modified as described above.

The lactic bacteria strains may be included in a food, pet food, cosmetic, or pharmaceutical composition, for example. Accordingly, the compositions are preferably a toothpaste, mouth rinse, gum, spray, beverage, candy, infant formula, ice cream, frozen dessert, sweet salad dressing, milk preparation, cheese, quark, yogurt, acidified milk, coffee cream, or whipped cream, for example.

In the compositions of the invention, the lactic bacteria strains may be included alone or in combination with milk derivatives, for example, in order to obtain synergistic preparations. Accordingly, these compositions for the health of the mouth comprise:

a lactic bacteria that is not part of the resident microflora of the mouth, which is capable of adhering directly to the pellicle of the teeth;

any forms of lactic glycopeptides, renneted milk, or bacteriocin.

Figure 2:
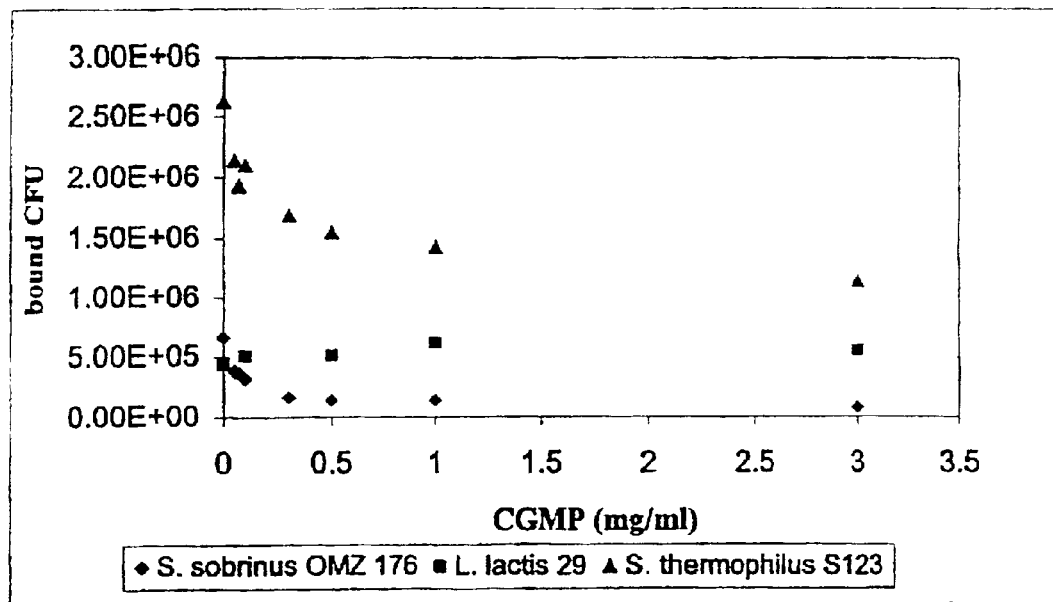
FIG. 2 represents the effect of CGMP on the adhesion to S-HA beads of *S. sobrinus* OMZ 176, *L. lactis* NCC2211, and *S. thermophilus* NCC1561.
Figure 3:
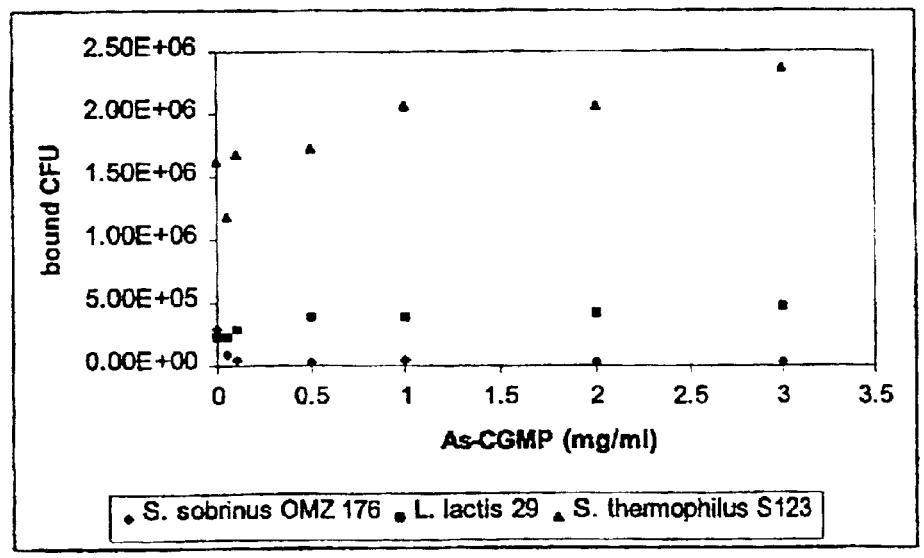
FIG. 3 represents the effect of As-CGMP on the adhesion to S-HA beads of *S. sobrinus* OMZ 176, *L. lactis* NCC2211, and *S. thermophilus* NCC 1561.

The lactic glycopeptides are preferably caseino-glycomacropeptides (CGMP), fluorinated or non-fluorinated micellar casein (which can be obtained as described in EP 0 604 802 and EP 0 748 591), or renneted milk. The caseino-glycomacropeptides are preferably added in a minimum amount of about 0.1%. It has also been shown that the caseino-glycomacropeptides do not prevent the lactic bacteria from adhering to the teeth pellicle (FIGS. 2 and 3).

Synergistic compositions may also be prepared by adding at least one bacteriocin which is active against Gram-positive oral bacteria. In this embodiment the oral hygiene compositions may comprise 0.00001 to 50%, and preferably from 0.00001 to 15% of purified bacteriocin, by weight of the composition. The bacteriocin is preferably variacin (EP 0759690).

To protect the composition from degradation, an oil-soluble antioxidant may also be included. Suitable antioxidants include the "tocopherols," butyl-hydroxyanisole (BHA), butyl-hydroxytoluene (BHT), and ascorbyl palmitate. The oil soluble antioxidant is present in amounts of from 0.005% to 0.5%, preferably 0.005% to 0.01% by weight of the composition.

Suitable abrasives for use in dentifrice compositions of the present invention include calcium carbonate, calcium aluminosilicate, alumina hydrates, alumina, zinc orthophosphate, plastic particles, and silica, of which silica is the preferred abrasive.

Compositions according to the invention will have a pH which is orally acceptable and within a range such that the activity of the lactic bacteria is not compromised. The pH may be in the range of 3.0 to 9.5, preferably in the range 3.5 to 6.5. The compositions of the invention may be prepared by conventional processes that comprise admixing the ingredients together in the appropriate relative amounts and finally, if necessary, adjusting the pH to the desired value.

The invention is further directed to a method for screening lactic bacteria capable of adhering to tooth. This method comprises the steps of:

(1) preparing monoclonal antibodies that recognize specific surface proteins of a lactic bacteria strain capable of adhering to the teeth, and (2) screening any lactic bacteria strain by using the monoclonal antibody of strain capable of adhering to the teeth.

The monoclonal antibodies are used as a tool to detect the said lactic bacteria strain among other strains growing nearby.

The present invention is not to be limited in scope by the specific embodiments described herein. Indeed, various modifications of the invention, in addition to those described herein, will become apparent to those skilled in the art from the foregoing description and accompanying figures. Such modifications are intended to fall within the scope of the claims. Various publications are cited herein, the disclosures of which are incorporated by reference in their entireties to the extent necessary for understanding the present invention. DNA manipulation, cloning and transformation of bacteria cells are, except where otherwise stated, carried out according to the textbook of Sambrook et al. (Sambrook et al., Molecular Cloning, A Laboratory Manual, Cold Spring Harbor Laboratory Press, U.S.A., 1989).

EXAMPLES

The examples are preceded by a brief description of the plasmids, strains, and the various media used, as well as the method for producing a monoclonal antibody.

The strains *S. thermophilus* S118 (NCC 1529), S123 (NCC 1561), *L lactis* subsp. *Lactis* 29 (NCC 2211), *L. lactis* subsp. *lactis* biovar dioacetylactis 69 (NCC 2225) were deposited under the Budapest Treaty at the Collection Nationale de Culture de Microorganismes (CNCM 1J,1984, CNCM 1-1985, CNCM 1-1986 and CNCM 1-1987, respectively), 25 rue du docteur Roux, 75724 Paris, France, on Mar. 3$^{rd}$, 1998. The strain *S. thermophilus* BF1 1116 (CNBL 1177) was deposited under the Budapest Treaty at the Belgian Coordinated Collections of Microorganisms LMG P-18997, K. L. Ledeganckstraat 35, B-9000 Gent, Belgium, on Jul. 5$^{th}$, 1999. All restrictions as to the availability of these deposits will be withdrawn upon first publication of this application or another application which claims benefit of priority to this application.

Example 1

Strains and Culture Conditions

More than 100 strains (belonging to the Nestle culture collection) were screened for their ability to attach to saliva-coated hydroxyapatite beads, and in particular the following 23 strains: *S. thermophilus* Y54 (NCC 2284), *S. thermophilus* Sfi6 (NCC 1971), *S. thermophilus Sfi*13 (NCC 2008), *S. thermophilus* Sfi21 (NCC 2038), *S. thermophilus* Sfi39 (NCC 2130), *S. thermophilus* Sfi42 (NCC 2145), *S. thermophilus* Sfi47 (NCC 2172), *S. thermophilus* S118 (NCC 1529), *S. thermophilus* S119 NCC 1536), *S. thermophilus* S122 (NCC 1554), *S. thermophilus* S123 (NCC 1561), *S. thermophilus* S126 (NCC 1587). *L. lactis* subsp. *cremoris* 15 (NCC 92), *L. lactis* subsp. *cremoris* 25 (NCC 1932), *L. lactis* subsp. *cremoris* 136 (NCC 2419), *L. lactis* subsp. *diacetylactis* 8 (NCC 1970), *L lactis* subsp. *diacetylactis* 28 (NCC 2057), *L. lactis* subsp. *diacetylactis* 69 (NCC 2225), *L. lactis* subsp. *diacetylactis* 80 (NCC 2272), *L. lactis* subsp. *lactis* 29 (NCC 2211), *L. lactis* subsp. *lactis* 50 (NCC 2224), *L. lactis* subsp. *lactis* 54 (NCC 2228), *S. macedonicus* 216 (NCC 2484).

The 5 oral strains, *S. sobrinus* OMZ 176, *S. oralis* OMZ 607, *A. naeslundii* OMZ 745, *V. dispar* OMZ 493 and *F. nucleatum* OMZ 596 were obtained from the Institute *für Orale Mikrobiologie and Aligemeine Immunologie, University of Zurich* and were cultured in FUM medium. in anaerobiosis (GasPackSystem, BBL) at 37° C.

All the strains were stored in glycerol at −20° C. and pre-cultured for 14 hours prior to use at their specific optimal temperature; *S. sobrinus* OMZ 176 grew in FUM medium lactococci and streptococci in M17 (Difco) except *S. thermophilus* NCC1529, S119, S122, NCC1561 and S126 that grew in Belliker (prepared by dissolution of 20 g tryptone, 5 g yeast extract, 2.5 g gelatine, 5 g dextrose, 5 g sucrose, 5 g lactose, 4 g NaCl, 0.5 g Ascorbic acid, and 10 g beef extract in 1 L of water).

For plate counting, *S. sobrinus* OMZ 176 was cultured in Mitis-Salivarius agar(Difco), *S. thermophilus* MCC1529, S119, S122, NCC1561, BF11116, and S126 in Belliker agar (prepared by adding to liquid Belliker 15 g of Bacto agar, Difco), and the remaining lactic bacteria strains in M17 agar (Oxoid).

Example 2

Production of Monoclonal Antibody

A monoclonal antibody would be used as a tool to detect *L. lactis* subsp. *lactis* NCC2211 among 5 oral strains growing together on S-HA discs and forming a biofilm that simulates dental plaque. Therefore the monoclonal antibody was tested against these strains to verify there was no cross-reaction. To this end, the monoclonal antibody is produced as described by Granato et al. "A mouse monoclonal IgE antibody anti-bovine milk lactoglobulin allows studies of allergy in the gastrointestinal tract., Clin. Exp. Immunol., 63. 703–710, 1986.

Example 3

Selection of Adherent Lactic Bacteria
Attachment to Saliva-coated Hydroxyapatite Beads (S-HA)

To select among the lactic bacteria dairy strains those strains that are able to attach to saliva-coated hydroxyapatite beads (S-HA), the procedure previously described by Neeser et al. (1994) was used with slight modification in that the bead washings were done with 150 μl volumes and Hyamine hydroxide was substituted with Benzethonium hydroxide (Sigma).

Briefly, all the strains were grown to the end of the log phase in FUM except *S. thermophilus* NCC1529, S119, S122, NCC1561, and S126 that were cultured in Belliker. *S.* sobrinus OMZ 176, L. lactis subsp. lactis NCC221 1, 50 and 54, S. thermophilus NCC1529. S119. S122. NCC1561. and S126 grew at 37° C. the remaining lactococci at 30° C. and the remaining streptococci at 42° C.

5 mg of hydroxyapatite beads (BDH Chemicals Ltd, Poole, England) were covered with 70 μl clarified saliva obtained from volunteers in the lab and prepared as previously explained (Neeser et al, 1994). Saliva coated beads were kept overnight at 4° C., then washed (first with distilled water and after with HEPES buffer) and finally inoculated with 100 μl of metabolically labeled bacterial suspension (bacteria had been grown in medium supplemented with 10 μCi/ml $^{14}$C acetic acid). Adhesion took place during 45 min at 37° C., then unbound bacteria were washed away and the attached cells directly counted in a LKB scintillation counter (type 1219 Rackbeta).

Adhesion percentages are expressed as radioactivity bound to the beads relative to the total radioactivity added to each well. All measurements were done in triplicate. Table 2 reports the percentages of adhesion to saliva-coated hydroxyapatite beads obtained for several screened strains and for S. sobrinus OMZ 176 (the reference strain).

TABLE 2

Percentages of Adhesion to Saliva-coated Hydroxyapatite Beads for Several Screened Strains.

| STRAIN | % ADHESION (±SD) |
|---|---|
| S. sobrinus OMZ 176 | 2.23 ± 0.49 |
| S. thermophilus Sfi42 (NCC 2145) | 0.08 ± 0.02 |
| S. thermophilus Sfi47 (NCC 2172) | 0.14 ± 0.04 |
| S. thermophilus NCC1529 | 2.89 ± 0.60 |
| S. thermophilus S119 (NCC 1536) | 0.15 ± 0.04 |
| S. thermophilus S122 (NCC 1554) | 0.93 ± 0.17 |
| S. thermophilus NCC1561 | 2.19 ± 0.50 |
| S. thermophilus S126 (NCC 1587) | 1.19 ± 0.56 |
| L. lactis subsp. diacetylactis 28 (NCC 2057) | 1.59 ± 0.17 |
| L. lactis subsp. diacetylactis NCC2225 | 1.96 ± 0.40 |
| L. lactis subsp. diacetylactis 80 (NCC 2272) | 1.20 ± 0.35 |
| L. lactis subsp. lactis NCC2211 | 2.85 ± 0.85 |

Four strains, S. thermophilus NCC 1529 (CNCM 1-1984), S. thermophilus NCC1561 (CNCM 1-1985), L. lactis subsp. lactis NCC221 I (CNCM 1-1986) (hereinafter L. lactis NCC2211) and L. lactis subsp. diacetylactis NCC2225 (CNCM 1-1987) showed adhesion values close to S. sobrinus OMZ 176.

L. lactis NCC2211 and S. thermophilus NCC1561 were chosen as the more promising candidates since they grow very well at 37° C., which is the temperature in the mouth, while L. diacetylactis NCC2225 has an optimal growth temperature of 30° C. In particular, L. lactis NCC2211 cannot grow on sucrose, but it can ferment a wide range of sugars, moreover other oral strain can provide glucose via their invertase.

Adhesion Saturation Curves

Figure 1B:
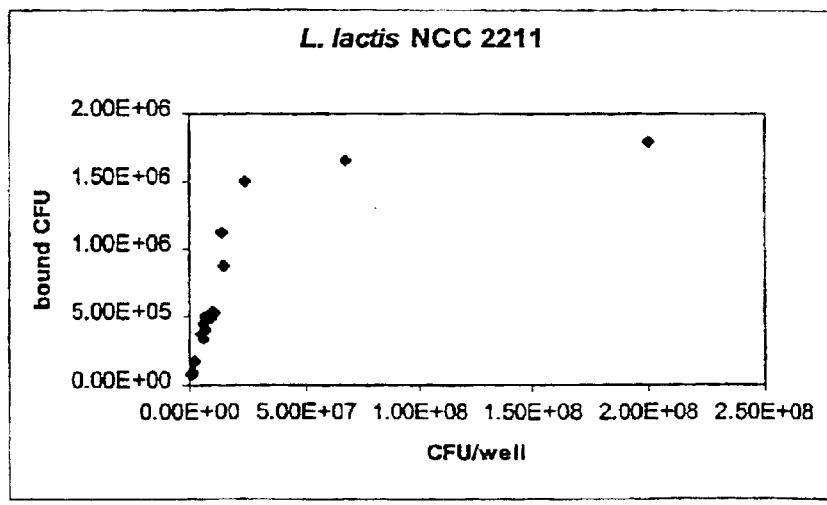
Figure 1C:
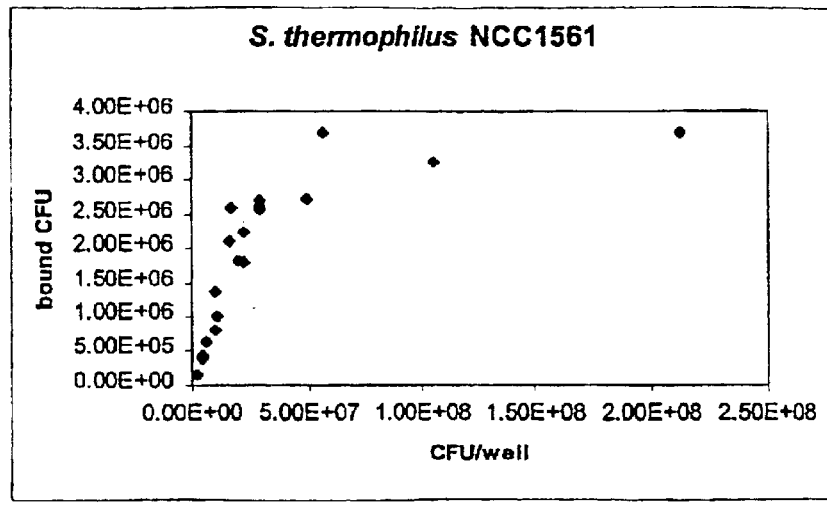

Curves of bound CFU versus CFU inoculated into the well were determined to verify if bead saturation could be obtained. The 50% saturation was obtained directly from the bending point of the curves. The adhesion saturation curves for S. sobrinus OMZ 176, L. lactis NCC2211, and S. thermophilus NCC 1561 were determined. They are shown in FIG. 1.

For each of the three strains the CFU number inoculated in the well to get 50% bead saturation and the corresponding number of bound CFU were directly deduced from the bending point of the curves and are given in the table 3.

TABLE 3

Number of CPU Inoculated Per Well to get 50% Bead Saturation.

| | cfu/well | Bound cfu | % adhesion |
|---|---|---|---|
| S. sobrinus OMZ 176 | 4.00 E+07 | 4.00 E+06 | 10% |
| L. lactis NCC2211 | 1.00 E+07 | 9.00 E-f-05 | 9% |
| S. thermophilus NCC1561 | 3.00 E+07 | 2.00 E+06 | 7% |

Example 4

Effect or Caseino-glycomacropeptides

The influence of CGMP on the adhesion of L. lactis NCC2211 and S. thermophilus NCC1561 was studied to verify the possibility of using CGMP to foster the predominance of one of these two strains over pathogenic strains, namely S. Sobrinus OMZ 176. Caseino-glycopeptide (CGMP) and its desialylated derivative (As-CGMP) were obtained from Nestec S. A., Lausanne (for their preparation see Neeser et al., 1994).

The dose-response effect was studied on the adhesion to S-HA beads by inoculating, in the well, 100 μl of bacterial suspension (CFU/ml corresponding to the 50% bead saturation previously calculated) which contained CGMP or AsCGMP in different concentrations and then performing the adhesion assay in the usual manner. Concentrations in the range 0.05 to 3 mg/ml were tested. No previous incubation of the bacteria in presence of CGMP or As-CGMP was done.

FIG. 2 provides the curves obtained for the three strains by plotting the number of bound cells versus increasing amounts of CGMP, the number of inoculated cells corresponds to 50% bead saturation formerly calculated for each strain. The strong inhibition observed in the case of S. sobrinus OMZ 176 confirms the previous results obtained by Neeser et al. (1994) and Schupbach et al., (J. Dent. Res., 75, 1779–1788, 1996).

FIG. 2 shows that 0.25 mg/ml produced 50% inhibition or the adhesion of S. sobrinus OMZ 176, while more than 2 mg/ml were necessary to have the same effect with S. thermophilus NCC1561. CGMP slightly enhances the adhesion of L. lactis NCC2211.

As in the case of CGMP, the desyalilated derivative inhibits the adhesion of S. sobrinus OMZ 176; only 0.05 mg/ml are needed to produce 50% decrease in the adhesion percentage. An CGMP does not influence L. lactis NCC2211 adhesion, while it slightly fosters the adhesion of S. thermophilus NCC1561 (FIG. 3).

Example 5

Toothpaste

Toothpaste is prepared by adding $10^5$ cfu/ml of at least one of the lactic bacteria strain CNCM 1-1984, CNCM 1-1985, CNCM 1-1986, CNCM 1-1987 or LMG P-18997 in a lyophilized form, to a mixture containing:

Cetyl pyridinum chloride 1.65%
Sorbitol (70% soln) 33.0%
Glycerin 25.0%
Sodium carboxymethyl cellulose 2.0%
Sodium fluoride 0.25%
Silica (RP 93) 26.3%
Thickening Silica (Sident 22) 8.1%

Sodium saccharine 0.5%

Poloxamer (Pluronic F 108) 3.2%

The toothpaste is intended for the prophylaxis or the treatment of dental caries, dental plaque, and periodontal infection.

Example 6

Ice Cream

A cream comprising 10.8% lactic fats, 13.5% milk solids (non fat), 0.3% Emulstab® SE30 and 0.3% Emulstab® foam (Grindsted, DK) is prepared and then pasteurized at 105° C. for 20 s, homogenized at 75° C. and 300 bar, cooled to 38° C., and inoculated with pre-cultures in MRS medium, taken in the exponential growth phase, at a rate of $10^7$ to $10^8$ cfu/ml of at least one of the lactic bacteria strain of CNCM 1-1984, CNCM 1-1985, CNCM 1-1986, CNCM 1-1987 or LMG P-18997. The cream is then fermented for 10 hours at 38° C. up to a pH of about 4.5. At the end of the fermentation, sucrose and glucose syrup is added thereto. The composition of the cream is presented in table 4 below. The mixture is then beaten, cooled to 4° C., stored at 4° C., and chilled to a degree of expansion of 95° C. by volume.

TABLE 4

Ice Cream Composition

| Ingredients | Composition (kg) | Fats (%) | Non-fat solids (%) | Sucrose (%) | Solids content (%) |
|---|---|---|---|---|---|
| Cream (35%) | 30.83 | 10.79 | 1.54 | | 12.33 |
| Powdered skimmed milk | 12.45 | | 11.95 | | 11.95 |
| Emulstab ® 5E30 | 0.41 | | | | 0.37 |
| Emulstab ® foam | 0.41 | | | | 0.36 |
| Water | 55.91 | | | | |
| Total: cream base | 100.00 | 10.79 | 13.49 | — | 25.01 |
| Cream base | 74.14 | 8.00 | 10.00 | — | 18.54 |
| Sucrose | 22.06 | | | 15.00 | 15.00 |
| Glucose syrup | 3.80 | | | | 3.00 |
| Fermented Ice cream | 100.00 | 8.00 | 10.00 | 15.00 | 36.54 |

Example 7

Yogurt

5 L MRS culture medium were sterilized for 15 min at 121° C. and then inoculated with 5% by volume of an active culture of at least one of the *S. Thermophilus* strains CNCM 1-1984, CNCM 1-1985, or LMG P-18997 containing approximately $10^9$ cfu/ml. After incubation for 8 h at 41° C., a starter containing $4.5 \times 10^8$ cfu/ml was obtained 5 L of reconstituted skimmed milk having a dry matter content of 10%, to which 0.1% yeast extract had been added, was sterilized for 15 min at 121° C. and inoculated with 2% of an active culture of commercial thickening *Streptococcus thermophilus* containing approximately $10^9$ cells/ml. After incubation for 4 h at 41° C., a starter containing $4.5 \times 10^8$ cells/ml was obtained.

One batch of whole milk containing 3.7% fats strengthened with 2.5% skimmed milk powder and then pasteurized for 30 min at 90° C. was then inoculated with 2% by volume of the starter or at least one of the CNCM 1-1984, CNCM 1-1985 or LMG P-18997 strains and 3% by volume of the starter of thickening *Streptococcus thermophilus*. The inoculated milk is stirred, poured into pots, and incubated for 4 h at 41° C. The resulting yogurt obtained has a good firm and smooth texture and is intended for the health of the mouth.

Example 8

Chewing Gum

A chewing gum for preventing or treating dental caries, dental plaque, or periodontal infection can be prepared adding an active culture of at least one of the *S. Thermophilus* strains CNCM 1-1984, CNCM 1-1985, or LMG P-18997 so that it contains approximately $10^4$ to $10^9$ cfu/g, to the following typical ingredients:

Xylitol 67.5%

Gum base 20%

Calcium carbonate 5%

Glycerin 3%

PluronicF127 2%

Cellulose gum 1%

Ballast compounds 0.5%

Flavor 1%

Example 9

Pet Food Composition

A pet food for mouth health is obtained by preparing a feed mixture made up of corn, corn gluten, chicken and fish meal, salts, vitamins, and minerals. The feed mixture is fed into a pre-conditioner and moistened. The moistened feed leaving the pre-conditioner is then fed into an extruder-cooker and gelatinised. The gelatinised matrix leaving the extruder is forced through a die and extruded. The extrudate is cut into pieces suitable for feeding to dogs, dried at about 110° C. for about 20 minutes, and cooled to form pellets which have a water activity of about 0.6. The pellets are sprayed with 3 coating mixtures. Each coating mixture contains an active culture of at least one of the *S. thermophilus* strains CNCM 1-1984, CNCM 1-1 985, or LMG P-18997 but one coating mixture uses hydrogenated soy fat as a coating substrate, one coating mixture uses water as a coating substrate, and one coating mixture uses protein digest as a coating substrate. The pellets contain approximately $10^4$ to $10^9$ cfu/g of the strains.

What is claimed is:

1. A method of treating or preventing dental caries, dental plaque, and periodontal infection in humans or animals comprising administering to the oral cavity of a human or animal one or more lactic bacteria that are one or more of the strains CNCM I-1984, CNCM I-1985, CNCM I-1986, CNCM I-1987, or LMG P-18997.

2. The method of claim 1, wherein the lactic bacteria have been genetically modified to have improved adherence to the pellicle of the teeth by insertion of the X17390 gene, the X14490 gene, or the X53657 gene.

3. The method of claim 1, further comprising administering the lactic bacteria in combination with one or more of milk, fermented milk, milk derivatives, or bacteriocin.

4. The method of claim 3, wherein the milk derivative comprises one or more of a caseino-glycomacropeptide, micellar casein, fluorinated micellar casein, or renneted milk.

5. The method of claim 1 wherein the lactic bacteria that are used for treating or preventing dental caries are administered by way of a composition that contains the lactic bacteria in an amount of $10^4$ to $10^4$ cfu/g in order to provide the pH of at least 5.5 when the composition is administered to the oral cavity of a human or animal.

6. The method of claim 5, wherein the composition further contains one or more of milk, fermented milk, or a milk derivative.

7. The method of claim 6, which further comprises a bacteriocin in an amount of 0.00001 to 50 percent by weight of the composition.

8. The method of claim 7, wherein the composition includes a milk derivative comprising one or more of a caseino-glycomacropeptide, micellar casein, fluorinated micellar casein, or renneted milk in an amount of at least 0.1 percent by weight of the composition.

9. The method of claim 5, wherein the composition further comprises one or more of an oil soluble antioxidant or an abrasive.

10. The method of claim 5, wherein the composition is in the form of a toothpaste, mouth rinse, gum, spray, beverage, candy, infant formula, ice cream, frozen dessert, sweet salad dressing, milk preparation, cheese, quark, yogurt, acidified milk, coffee cream or whipped cream.

* * * * *